United States Patent
Nickel

(10) Patent No.: US 9,789,284 B2
(45) Date of Patent: Oct. 17, 2017

(54) URINARY CATHETER ASSEMBLY AND METHOD

(71) Applicant: The United States of America as Represented by The Department of Veterans Affairs, Washington, DC (US)

(72) Inventor: Eric Nickel, Minneapolis, MN (US)

(73) Assignee: Department of Veterans Affairs, Washington, DC (US)

( * ) Notice: Subject to any disclaimer, the term of this patent is extended or adjusted under 35 U.S.C. 154(b) by 408 days.

(21) Appl. No.: 14/579,795

(22) Filed: Dec. 22, 2014

(65) Prior Publication Data

US 2016/0175570 A1 Jun. 23, 2016

(51) Int. Cl.
*A61M 27/00* (2006.01)
*A61M 25/01* (2006.01)

(52) U.S. Cl.
CPC ..... *A61M 25/0111* (2013.01); *A61M 25/0119* (2013.01); *A61M 2210/1089* (2013.01)

(58) Field of Classification Search
CPC .......... A61M 25/0111; A61M 25/0119; A61M 2210/1089
See application file for complete search history.

(56) References Cited

U.S. PATENT DOCUMENTS

| | | | |
|---|---|---|---|
| 3,421,509 A * | 1/1969 | Fiore | A61M 25/0017 206/364 |
| 5,779,670 A * | 7/1998 | Bidwell | A61M 25/0017 604/172 |
| 6,117,120 A | 9/2000 | Heininger | |
| 2005/0124978 A1 | 6/2005 | Kim | |
| 2007/0270734 A1 | 11/2007 | Crisp | |
| 2012/0325692 A1 | 12/2012 | Tanghoj et al. | |

FOREIGN PATENT DOCUMENTS

| | | |
|---|---|---|
| EP | 0909249 B1 | 4/2005 |
| WO | 2016106240 A1 | 6/2016 |

OTHER PUBLICATIONS

International Search Report and Written Opinion for related International Application No. PCT/US2015/067164 dated Apr. 14, 2016 in 13 pages.

* cited by examiner

*Primary Examiner* — Leslie Deak
*Assistant Examiner* — Kai Weng
(74) *Attorney, Agent, or Firm* — Procopio Cory Hargreaves and Savitch LLP; Pattric Rawlins; Katherine Proctor

(57) ABSTRACT

A urinary catheter is configured to avoid sliding contact between the outer surface of a catheter tube and the urethra wall. A flexible tubular membrane extends through the catheter tube and has a proximal end secured to an anchor outside the urethra as the catheter tube moves into the urethra, pulling the membrane through the proximal end of the tube so it inverts and covers the outer surface of the tube. Alternatively, a catheter tube of flexible material has a proximal end secured to the anchor, and the catheter tube turns inside out as it is inserted, forming a double wall reflected tube with a proximal reflection point. The sterile interior surface of the membrane or tube becomes the external surface facing the urethral wall as the catheter is deployed, and this external surface maintains static contact with the urethral wall as the catheter is advanced or retracted.

12 Claims, 3 Drawing Sheets

URINARY CATHETER ASSEMBLY AND METHOD

BACKGROUND

Field of the Invention

The present invention is generally related to urinary catheters as used for draining the bladder of patients suffering from urinary retention or by disabled individuals who have no way of controlling urination, and is particularly concerned with a urinary catheter which allows voiding of the bladder with reduced risk of urinary tract infection.

Related Art

Persons with urinary retention due to spinal cord injury, multiple sclerosis, prostate enlargement, or the like use disposable urinary catheters, referred to as intermittent catheters, to void their bladder. The process of catheterization can be messy and sometimes leads to urinary tract infections.

The state of the art is to slide a flexible plastic tube up the urethra and into the bladder. The tube is often heavily lubricated in an effort to reduce damage to the urethra due to surface abrasion caused by the sliding of the catheter against the urethral walls. The state of the art has changed relatively little in general method with most recent developments occurring in the area of coatings, lubrication, and packaging, for example as described in WO 1998011932, EP0909249, WO 2013075725, US 2012/0325692, WO 2002011810, EP 1786591, EP 2226042, WO 2001062315, and EP 1131022. All of these catheters rely on the catheter (usually with lubricant coating) being forcefully slid through the urethra with sliding of the catheter tube against the wall of the urethra. Micro trauma from this sliding can be a source of urinary tract infection. The exterior surface of the catheter can become contaminated with bacteria when sliding through the male urethral meatus which then are carried up into sterile regions of the urethra and into the bladder, potentially causing urinary tract infection. The risk of infection is reduced by use of an insertion tip which opens up the entry of the urethra, with the catheter sliding through the insertion tip into the urethra. However, bacteria are still present at the end of the insertion tip and can be picked up and carried by the leading end of the catheter into the bladder.

SUMMARY

In order to reduce or avoid the risk of urinary tract infections as well as damage to the urethra during catheterization, a urinary catheter assembly is provided which avoids direct sliding contact between the catheter tube and the urethra wall and protects the urethra and bladder from bacteria and other contaminants.

In one aspect, a urinary catheter assembly comprises a catheter tube having an outer surface, a proximal end and a distal end, and a sterile inner lumen. A flexible inner portion is disposed between the outer surface of the catheter tube and the sterile inner lumen and has a sterile inner surface facing the sterile inner lumen, and a proximal end secured to an anchor which is located at least partially outside the urethra during catheterization. The flexible inner portion of the catheter tube is inverted as the catheter tube is inserted through the urethra and into the bladder so that the sterile inner surface faces outwards towards the urethra. In one aspect, the anchor comprises an introducer or applicator tip having a central opening and configured to guide the catheter tube through the central opening and into a patient's urethra. The applicator or introducer tip has an annular flange and a tapered end designed to open the external opening of the urethra or urethral meatus.

In one aspect, the sterile inner portion comprises a flexible tubular membrane extending inside the catheter tube and not secured to the catheter tube, and having a proximal end portion extending out of the proximal end of the catheter tube and secured to the anchor or introducer tip. The flexible tubular membrane is pulled out over the proximal end of the catheter tube as the catheter tube is inserted through the urethra and into the bladder, and inverts to form a sheath over the entire length of the outer surface of the catheter tube inside the urethra with the sterile inner surface of the flexible tubular membrane facing the wall of the urethra. The tubular membrane slides freely relative to the catheter tube, and may extend from the proximal end to the distal end of the catheter tube, terminate short of the distal end, or extend out of both ends of the tube. In one aspect, the tubular membrane is at least twice the length of the catheter tube so that it projects out of the tube at all times and the distal end can be used to pull both the tubular membrane and the catheter tube out of the urethra after use.

In one aspect of an insertion method using the catheter assembly, the tapered end of the introducer tip is first engaged in the external urethra opening, and the proximal end of the catheter tube is inserted through the applicator or inserter tip and into the urethra. At the same time, a proximal end portion of the flexible membrane is pulled out of the tube due to the attachment of the end of the membrane to the annular flange or other anchor outside the urethra, and folds back or inverts over the proximal end and outer surface of the catheter tube, providing a barrier between the catheter tube and inner wall of the urethra. The sterilized inner surface of the tubular membrane thus faces outward towards the urethral wall as the membrane is fed through the tube and folds back over the outer surface of the catheter tube, protecting the urethra from contact with the more rigid catheter tube and reducing the risk of trauma.

Because the tubular membrane does not slide up the urethra but stays in the same position as soon as it is deployed, a sterile environment is maintained during both application and removal and the risk of bacteria being carried up the urethra to the bladder is reduced or eliminated. Once the catheter tube has been inserted through the urethra into the bladder, urine is voided through the catheter tube into a suitable container or pouch associated with the distal end of the tube or directly into a toilet. After voiding, the catheter tube is retracted from the urethra while the tubular membrane remains as a barrier between the moving tube and urethra, reversing the application process and still avoiding sliding of the relatively rigid catheter tube against the urethra wall. The tubular membrane is also pulled progressively out of the urethra through the catheter tube during retraction of the catheter tube. Thus, a sterile environment is maintained at all times during deployment, voiding of the bladder, and removal of the catheter tube, tubular membrane, and insertion tip or applicator. In one embodiment, the projecting distal end portion of the tubular membrane is pulled out, which in turn pulls the catheter tube out of the urethra as the tubular membrane reflects or reverts back into the catheter tube lumen.

According to another aspect, the flexible inner portion is secured to the catheter tube and integrally formed with the tube, and the proximal end of the catheter tube is secured to the anchor such as an applicator tip. The flexible catheter tube is configured to reflect or fold back on itself to form a double wall tube as it is inserted through the applicator tip into the urethra, due to the attachment of the proximal end to the anchor as well as the flexibility of the material forming the tube. The tube inverts or turns inside out against the urethra with the sterile, inner surface of the tube facing outwards along the length of the urethra. This forms a double-wall reflected tube with a rounded reflection point at its proximal end which advances through the urethra into the bladder. The tube material and wall thickness is sufficient to allow the tube to invert or fold back on itself at the reflection point, while being stiff enough to permit continued advancement of the catheter tube all the way up the urethra and into the bladder without collapsing the tube.

In both alternatives, the outer surface of the catheter tube does not slide against the wall of the urethra either during application or during removal. In the tube and film example, the inner, sterile surface of the tubular film or membrane is folded back to face the urethral wall at all times during both insertion and removal, unrolling or inverting over the outer surface of the relatively rigid catheter tube during insertion and reverting back into the lumen of the catheter tube as it is pulled back out of the urethra. In the unitary flexible tube example, the inner, sterile surface of the tube faces outwards as the tube rolls back on itself during insertion and the process is reversed on removal. In both cases, the sterile interior of the film or tube becomes the outside that is in contact with the urethra during insertion, maintaining a sterile environment and reducing the risk of infection or trauma. There is no sliding against the urethra in either version, considerably reducing or eliminating the risk of bacteria being carried up the urethra into the bladder. In the tube and film version, the catheter tube is the only sliding part and is shielded within the tubular membrane. The tubular film or membrane is continuously fed out of the end of the catheter tube and unrolls or is inverted into the urethra without any sliding against the urethral surface. In the unitary flexible tube version, there is also no sliding movement. Instead, the tube simply turns inside out to form a double wall tube in the urethra, and statically contacts the urethra with its inner, sterile surface facing outwards. This can help reduce the risk of urinary tract infections in patients who use intermittent catheterization for voiding the bladder.

Other features and advantages will become more readily apparent to those of ordinary skill in the art after reviewing the following detailed description and the accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments disclosed herein provide for a urinary catheter assembly which can be introduced into the urethra without sliding, reducing the risk of micro trauma to the urethral wall and transport of bacteria and other infectious agents from the urethral meatus into the urethra and bladder, and also considerably reducing the risk of urinary tract infection. For example, one urinary catheter assembly disclosed herein has a durable tubular membrane or film which extends inside a catheter tube adjacent the inner surface of the tube and out of the proximal end of the tube, with a proximal end of the tubular membrane secured to an anchor such as an applicator tip outside the urethra. As the catheter tube is inserted, the tubular membrane folds over the proximal end of the tube and is inverted over the outer surface of the tube to form a sheath, with the sterile inner surface of the membrane facing outwards to maintain a sterile field during catheter insertion.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention.

Figure 1:
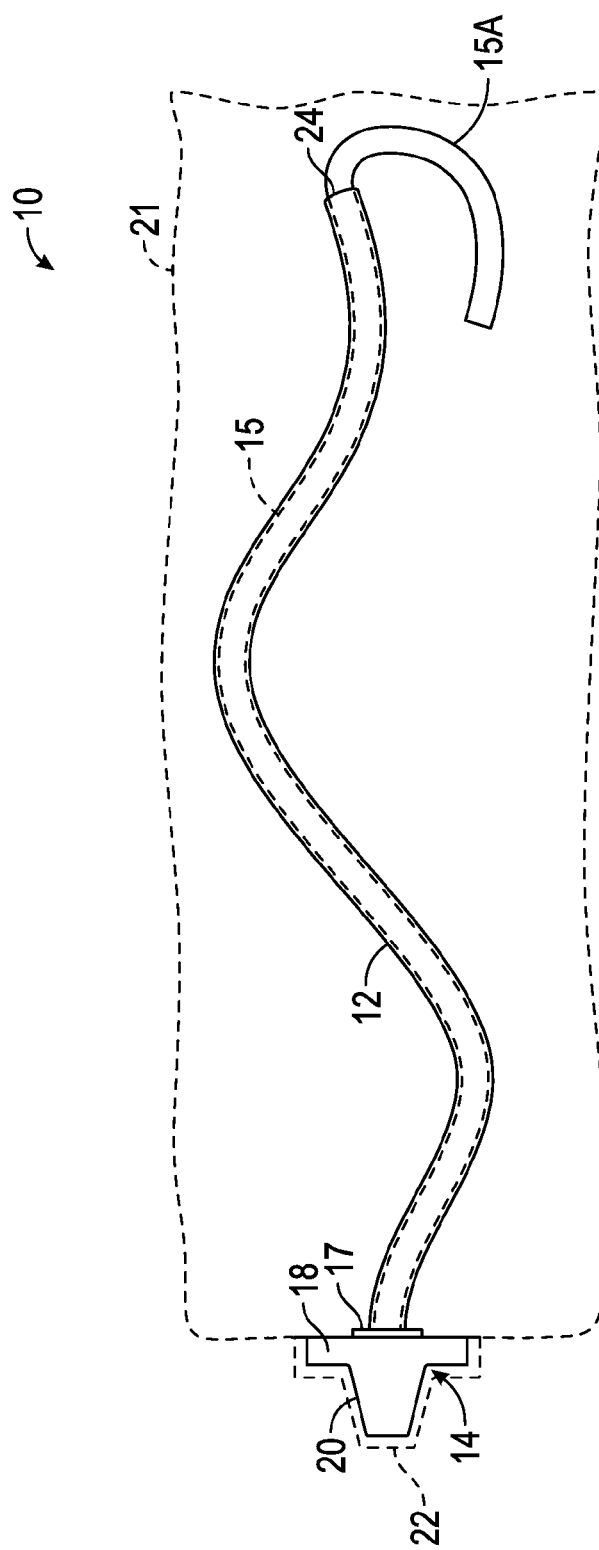
FIG. 1 is a top plan view of one embodiment of a urinary catheter assembly.
Figure 2:
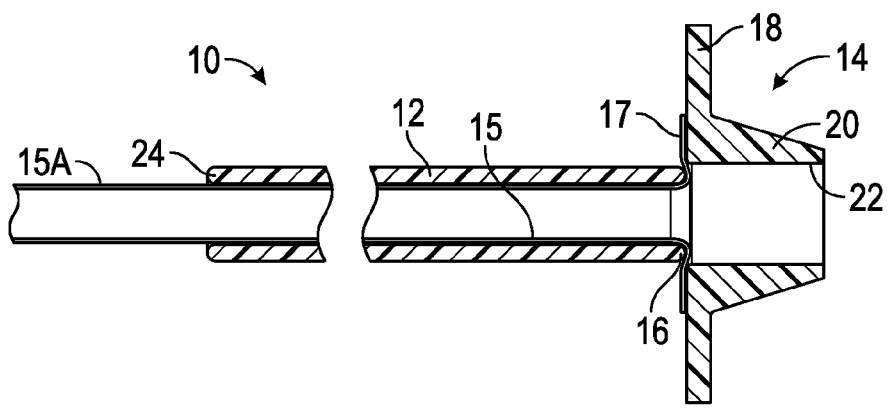
FIG. 2 is a longitudinal cross-sectional view of the catheter assembly of FIG. 1, partially cut away.

FIGS. 1 to 3B illustrate a first embodiment of a urinary catheter assembly 10 which comprises a catheter tube 12 which may be similar to commercially available intermittent catheter tubes in one embodiment, an applicator or introducer tip 14 designed to open the external opening of the urethra (the urethral meatus) and guide the catheter tube into the urethra, and a tubular film or membrane 15 which extends along the inner surface of the catheter tube and out of the proximal end 16 of the catheter tube with the proximal end 17 of membrane 15 secured to an anchor such as applicator tip 14, as illustrated in FIG. 2 and in dotted lines in FIG. 1. This effectively forms a two part catheter device comprising outer catheter tube 12 and inner tubular membrane 15. Membrane 15 is not secured to the catheter tube, only to the applicator tip 14 at its proximal end. Applicator tip 14 may be similar to commercially available urinary catheter applicators in one embodiment. A suitable pouch or container of a conventional nature may be connected to the distal end 21 of the assembly for receiving urine when the bladder is voided, or the urine may be voided directly into the toilet, as is known in the field. In one example, catheter assembly 10 is initially sealed inside a sterile bag or pouch 21 as shown in dotted lines in FIG. 1, with introducer tip 14 located outside the bag 21 and sealed or secured inside an external cap as illustrated by dotted line 22 in FIG. 1.

However, different urine collection arrangements may be used in other embodiments, as is known in the intermittent catheter field.

Introducer or applicator tip 14 has an annular ring or flange 18 and a tapered tip portion 20 extending from the flange and designed to open the external end of the urethra, while the flange 18 prevents the applicator or introducer tip from entering the urethra beyond a given point. The introducer tip has a central through bore or opening 22 of diameter slightly greater than the external diameter of the catheter tube 12, so that the tube 12 can be inserted through introducer tip 14 into the urethra. The proximal end 17 of membrane 15 is secured or anchored to the outer surface of annular flange 18, as best illustrated in FIG. 2, while the remainder of the tubular membrane extends through the proximal end 16 of the catheter tube along the inner surface of tube 12. In the illustrated embodiment, tubular film or membrane 15 is longer than the catheter tube and a portion 15A of the membrane extends out of the distal end of the catheter tube, as illustrated in FIG. 1. In one embodiment, the tubular membrane is double the length of the catheter tube or longer so part of the membrane still extends out of the distal end of the catheter tube after deployment of the catheter tube into a patient's urethra. Alternatively, film or membrane 15 may be the approximately the same length or shorter than tube 12, so that it extends up to the distal end 24 of tube 12 or to a location close to the distal end of the tube prior to insertion of the catheter tube, as long as the length is sufficient to allow the membrane to cover essentially double the distance traveled by the catheter tube as it is inserted into the urethra.

The tubular membrane has a wall thickness much less than the wall thickness of the catheter tube and is made of a sterile, flexible thin film material which is tear resistant. In one example, the tubular membrane or film may be made of the type of material used to make condoms such as polyurethane, silicone rubber, or latex, and may have a wall thickness similar to that of a condom (around 0.02 mm to 0.1 mm). Other possible materials for tubular membrane 15 are typical sterile plastic film materials used to make surgical gloves, food service gloves or the like. The film may be reinforced by thin filaments or fibers running longitudinally or woven into a mesh to provide resistance to longitudinal stretching during application. Possible materials for such fibers may be carbon, glass, aramid plastics, or the like.

Figure 3A:
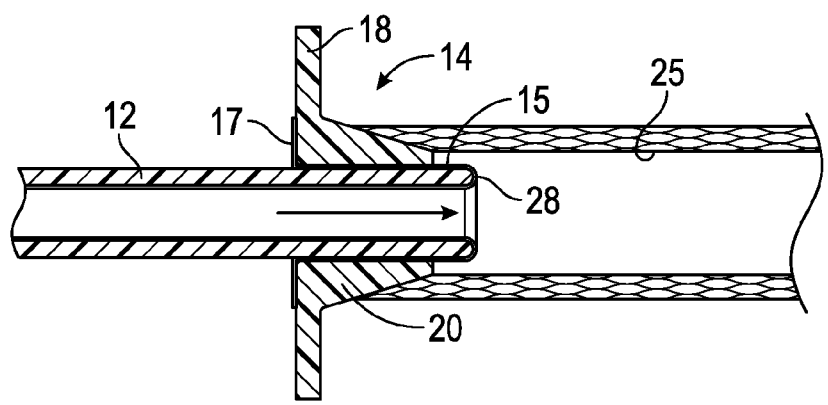
FIG. 3A is a cross-sectional view of a proximal end portion of the catheter assembly of FIGS. 1 and 2 at an initial stage of insertion into the urethra, illustrating the proximal end portion of the catheter tube extending through the catheter tip into the urethra, with the tubular sterile film being pulled out of the proximal end of the catheter tube and folding back over the outer surface of the catheter tube as the tube is inserted.
Figure 3B:
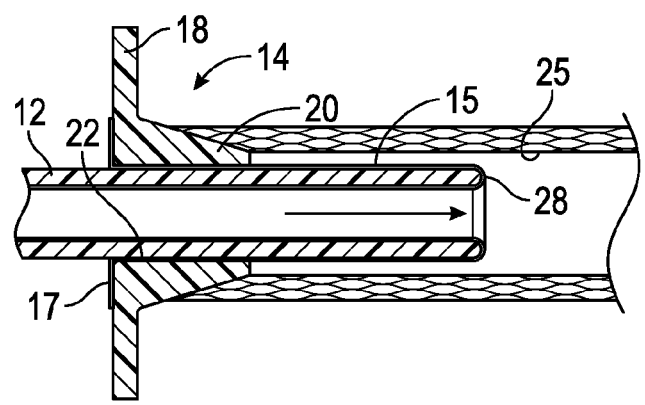
FIG. 3B is a cross-sectional view similar to FIG. 3A and illustrating the catheter tube inserted farther into the urethra with the film rolling farther out of the proximal end of the tube and back over the outer surface of the tube.

As the catheter tube 12 is inserted through the introducer tip 14 and into the urethra 25, as illustrated in FIG. 3A, one end of the durable tubular membrane 15 remains anchored to the introducer tip at 17. The membrane is therefore drawn up and out of the proximal end 16 of the catheter tube as the tube is inserted, and rolls back over the outer surface of the tube so that the tubular membrane is turned inside out or inverted over the outer surface of the catheter tube, with the inner, sterile surface 26 of tubular membrane 15 exposed and pressed against the urethral wall along the entire length of the catheter tube currently extending into the urethra. FIG. 3B illustrates a later stage with the catheter tube inserted farther into the urethra with more of the tubular film or membrane inverted or reflected back on itself at reflection point 28 to cover the proximal end and outer surface of the catheter tube. Insertion is continued until the proximal end 16 of catheter tube 12 is located inside the bladder. The tubular film 15 is of sufficient length so that a portion of the membrane 15 remains inside the catheter tube when the proximal end of the tube reaches the bladder. In one embodiment, the length of film 15A extending out of the distal end of tube 12 prior to insertion is sufficient to ensure that the distal end is still outside the catheter tube when the tube is fully inserted. Where the film material is reinforced with fibers, the fiber is of a material which is able to reflect back on itself with a small bend radius without breaking, while the film material expands radially as it reflects back over the proximal end of the catheter tube.

Once the proximal end of the catheter tube is located in the bladder, at least part or all of the inner surface of the catheter tube as well as the proximal end and the entire length of the outer surface of catheter tube extending from the bladder to the applicator tip are covered by the tubular film or membrane. The film effectively acts as a sheath covering some or all of the inner surface of the catheter tube and the entire length of the outer surface of the catheter tube inside the urethra and bladder, with the sterile inner surface of the sheath facing outwards and protecting the urethra and bladder from potential contaminants on the outer surface or proximal tip of the catheter tube.

In the embodiment of FIGS. 1 to 3B, the exposed region of the membrane 15 acts as a barrier or sheath between the catheter tube and the urethra, preventing or reducing the risk of micro trauma to the urethra surface. The sterile lumen of the membrane becomes the external surface when deployed, maintaining a sterile environment within the urethra. This arrangement also reduces discomfort during catheter insertion, since sliding movement between the catheter tube and inner surface of the urethra is eliminated. There is no moving surface against the urethra. Instead, the film is simply drawn up the catheter until it is exposed and pressed against the urethral wall, and turns back on itself or inside out in a similar manner to a sock turned inside out, preventing or reducing the risk of bacteria or other infectious agents or contaminants being carried from the outer end portion of the urethra into the bladder. The film is effectively unrolled into the urethra, maintaining static contact with the urethra during deployment and removal of the catheter tube. During deployment, the sterile interior of the film becomes the outside that is in contact with the urethra, and is the only part of the catheter assembly that contacts the urethra during insertion, apart from the applicator tip.

After voiding the bladder, the catheter tube is withdrawn from the urethra, reversing the application process while the flexible membrane continues to protect the urethral wall from the tube sliding against the wall. The sterile internal surface or lumen of the tubular membrane continues to act as a barrier between the outer surface and proximal tip of catheter tube and the urethral wall. The tubular film or membrane may be retracted with the catheter tube by pulling the distal end of the tubular film where it is of sufficient length to project out of the distal end of the catheter tube after insertion. This in turn pulls out the catheter tube as the film reflects or reverts back within the catheter tube lumen.

The catheter assembly of FIGS. 1 to 3B can help to prevent or reduce the risk of micro trauma or bladder infections in patients using intermittent catheterization for voiding the bladder, and also decreases patient discomfort during catheterization.

Although the proximal end of the flexible membrane is secured to the applicator tip in the illustrated embodiment, it may be secured at some other anchor or point outside the urethra in other embodiments. For example, in another embodiment it may be secured to the opening in collection bag or pouch 21 of FIG. 1 through which catheter tube is extended for deployment.

Figure 4:
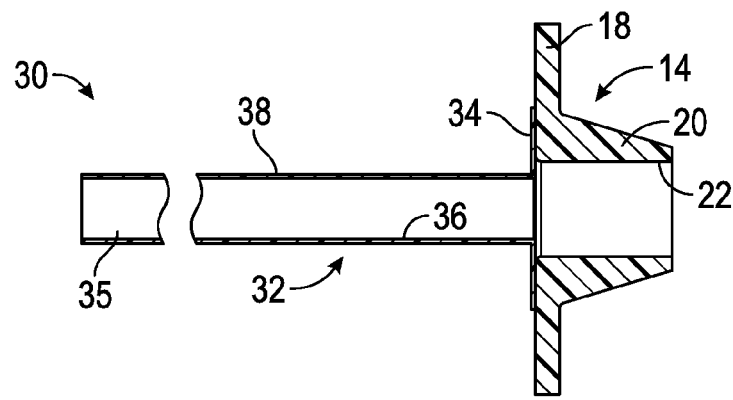
FIG. 4 is a cross-sectional view of a second embodiment of a urinary catheter assembly, partially cut away.
Figure 5A:
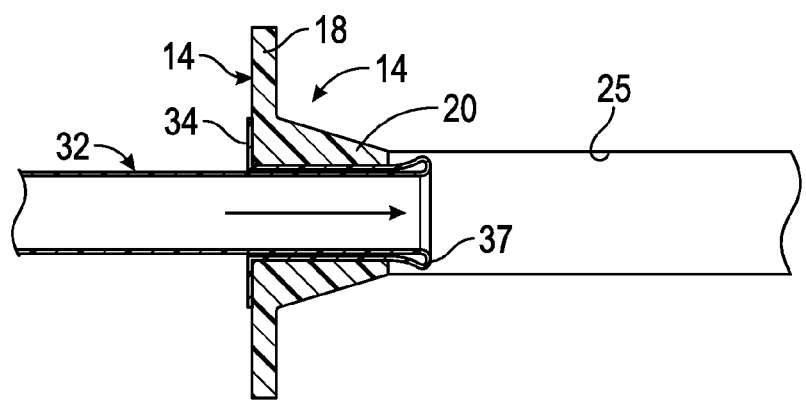
FIG. 5A is a cross-sectional view illustrating the catheter tube of FIG. 4 extending through the catheter tip and rolling back over itself to form a double walled tube extending into the urethra.
Figure 5B:
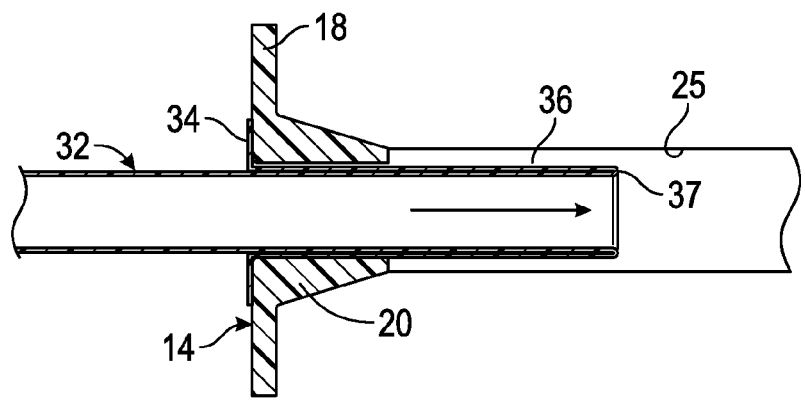
FIG. 5B is a cross-sectional view similar to FIG. 5A and illustrating the double walled catheter tube inserted farther into the urethra.

FIGS. 4 to 5B illustrate a second embodiment of a catheter assembly 30 for use in intermittent catheterization. In this embodiment, the two part catheter device of the first embodiment comprising a catheter tube and inner tubular flexible membrane are replaced with a single catheter tube 32 of flexible material thicker than the flexible membrane 15. The proximal end 34 of tube 32 is secured to the outer surface of annular flange 18 of applicator tip 14, which is similar or identical to the applicator tip of the first embodiment. Tube 32 has a sterile internal lumen 35. A conventional intermittent catheter tube is typically made of a polymer which is soft enough to flex with the urethra yet stiff enough to allow the user to push it up the urethra and into the bladder. The catheter tube 32 of this embodiment is designed to be more flexible than the conventional intermittent catheter, and may be of an elastomeric polymer material having a thinner wall than a conventional catheter tube. The material of tube 32 is designed to be relatively rigid in a longitudinal direction, to allow sufficient stiffness for insertion through the urethra into the bladder, while being flexible in a radial direction. In one example, the tube 32 may be of a silicone rubber or other plastic or polymeric material with suitable reinforcing fibers which are bendable but rigid in a longitudinal direction, such as are used in hydraulic hose material.

As the flexible tube 32 is inserted into the urethra, it inverts or folds back on itself due to the attachment of the proximal end 34 to flange or anchor 18, and turns inside out, continuing to fold back against the urethra with the sterile, inner surface 36 of the tube facing outwards along the length of the urethra until the tube reaches the bladder. As the catheter is inserted, it does not slide, but simply rolls back on itself or "unrolls" into the urethra, statically contacting the urethral wall. The tube material and wall thickness is sufficient to allow the tube to fold back on itself to form a double-wall reflected tube with a rounded reflection point or tip 37, as illustrated in FIG. 5A and 5B, while being stiff enough to permit continued advancement of the catheter tube all the way up the urethra and into the bladder without collapsing the tube. Once the bladder is voided through the tube 32 into a suitable container, the process is reversed with the tube re-inverting or rolling back out of the double walled condition into a single tube as it is pulled out through the urethra. At all times, the sterile inner surface of the tube is the only part exposed to the urethral wall, with the external or outer surface 38 shielded from the interior of the urethra.

Since the catheter tube in this embodiment is doubled back on itself to form a double wall during insertion, the length of the tube is approximately twice the length of a conventional catheter tube, i.e. around two inches for a female catheter, and around twenty inches or more for a male catheter. It may also have a reduced wall thickness as compared to a conventional catheter tube.

In both examples described above, the outer surface of the catheter tube does not slide against the wall of the urethra either during application or during removal. In the tube and film embodiment of FIGS. 1 to 3B, the inner, sterile surface of the tubular film or membrane faces the urethral wall at all times during both insertion and removal, unrolling over the outer surface of the relatively rigid catheter tube during insertion and continuing to cover the tube as it is withdrawn. In the double wall flexible tube embodiment of FIGS. 4 to 5B, the inner, initially sterile surface of the tube faces outwards as the tube rolls back on itself during insertion and the process is reversed on removal. In both cases, the sterile interior of the film or tube becomes the external surface that is in contact with the urethra. In each case, this external surface maintains static contact with the urethral wall as the catheter is advanced or retracted, maintaining a sterile environment and reducing the risk of infection or trauma. This can help reduce the risk of urinary tract infections in patients who use intermittent catheterization for voiding the bladder, such as persons with urinary retention due to spinal cord injury, multiple sclerosis, prostate enlargement, or the like.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

I claim:

1. A urinary catheter assembly, comprising:
   a catheter tube having an outer surface, a proximal end and a distal end, and a sterile inner lumen;
   an anchor which is located at least partially outside a urethra during catheterization;
   a flexible inner portion disposed between the outer surface of the catheter tube and the inner lumen and having a sterile inner surface facing the sterile inner lumen and a proximal end secured to the anchor, wherein the flexible inner portion having a sterile inner surface is an integral part of the catheter tube and wherein the proximal end of the catheter tube is secured to the anchor and the catheter tube is configured to fold back on itself to form a double-walled tube with a rounded reflection point at the proximal end of the double-walled tube when the catheter tube is inserted through the urethra;
   whereby the sterile inner surface of the flexible inner portion of the catheter tube is inverted and faces the urethra as the catheter tube is inserted through the urethra.

2. The catheter assembly of claim 1, wherein the anchor comprises an applicator tip having a central opening and configured to guide the catheter tube through the central opening and into the urethra.

3. The catheter assembly of claim 1, wherein the flexible inner portion comprises a tubular film of material selected from the group consisting of silicone rubber, polyurethane, polyethylene, polypropylene, and latex.

4. The catheter assembly of claim 1, wherein the flexible inner portion extends along the entire length of the inner surface of the catheter tube.

5. The catheter assembly of claim 1, wherein the flexible inner portion has a length greater than the length of the catheter tube and has a distal end portion which extends out of the distal end of the catheter tube.

6. The catheter assembly of claim 5, wherein the flexible inner portion has a length at least twice the length of the catheter tube.

7. The catheter assembly of claim 1, wherein the catheter tube has a length at least double the length of a standard intermittent catheter tube.

8. The catheter assembly of claim 1, wherein the catheter tube has a length of around two inches and is a female urinary catheter.

9. The catheter assembly of claim 1, wherein the catheter tube has a length of at least twenty inches and is a male urinary catheter.

10. The catheter assembly of claim 1, wherein the anchor comprises an applicator tip having a central opening and configured to guide the catheter tube through the central opening and into the patient's urethra, and the proximal end of the catheter tube is secured to a portion of the applicator tip which is outside the urethra during insertion of the catheter tube.

11. A urinary catheterization method, comprising:
   anchoring a proximal end of a flexible catheter tube to an anchor outside a urethra;
   urging the catheter tube into the urethra with the catheter tube folding back on itself due to the attachment of the proximal end to the anchor outside the urethra, forming a double-wall reflected tube with a rounded reflection point forming the proximal end of the double-wall tube, whereby an inner sterile surface of the catheter tube faces outward towards the urethra during insertion of the double-wall reflected tube through the urethra;
   advancing the double-wall reflected tube until the rounded reflection point is inside the bladder;
   draining the patient's bladder into a container in communication with a distal end of the catheter tube; and
   retracting the catheter tube from the bladder and urethra with the double walled tube rolling back out of the double walled condition into a single tube as it is retracted out of the urethra.

12. The method of claim 11, further comprising inserting a forward end portion of an applicator tip into an outer end of the urethra with the remainder of the applicator tip engaged outside the urethra prior to insertion of the catheter tube, the portion of the applicator tip outside the urethra comprising the anchor to which the proximal end of the catheter tube is anchored, wherein the step of urging the catheter tube into the urethra comprises first urging the catheter tube through a central guide bore in the applicator tip and into the urethra.

* * * * *